(12) United States Patent
Hilkert et al.

(10) Patent No.: US 7,213,443 B2
(45) Date of Patent: May 8, 2007

(54) PROCESS AND APPARATUS FOR PROVIDING GAS FOR ISOTOPIC RATIO ANALYSIS

(75) Inventors: Andreas Hilkert, Delmenhorst (DE); Reinhold Pesch, Weyhe (DE)

(73) Assignee: University of Bern, Bern (CH)

( * ) Notice: Subject to any disclaimer, the term of this patent is extended or adjusted under 35 U.S.C. 154(b) by 0 days.

(21) Appl. No.: 10/417,917

(22) Filed: Apr. 16, 2003

(65) Prior Publication Data

US 2003/0226394 A1     Dec. 11, 2003

(51) Int. Cl.
*G01N 30/02* (2006.01)
*G01N 1/00* (2006.01)

(52) U.S. Cl. .................... 73/23.37; 73/23.41
(58) Field of Classification Search ........... 73/23.37, 73/23.42, 23.41; 250/288
See application file for complete search history.

(56) References Cited

U.S. PATENT DOCUMENTS

| | | | |
|---|---|---|---|
| 3,996,003 A | 12/1976 | Fine et al. | |
| 4,014,793 A | 3/1977 | Tesarik et al. | |
| 4,046,510 A | 9/1977 | Becker et al. | |
| 4,055,987 A | 11/1977 | McFadden | |
| 4,112,297 A | 9/1978 | Miyagi et al. | |
| 4,886,528 A | 12/1989 | Aaltonen et al. | |
| 4,916,313 A * | 4/1990 | Hall et al. | 250/282 |
| 5,012,052 A * | 4/1991 | Hayes | 250/288 |
| 5,090,256 A | 2/1992 | Issenmann | |
| 5,102,805 A | 4/1992 | Baughman et al. | |
| 5,308,979 A | 5/1994 | Villa-Aleman | |
| 5,314,827 A | 5/1994 | Schmidt et al. | |
| 5,331,160 A | 7/1994 | Whitt | |
| 5,366,900 A | 11/1994 | Conboy et al. | |
| 5,643,799 A | 7/1997 | Atwater et al. | |
| 5,661,038 A | 8/1997 | Brenna et al. | |
| 5,672,516 A | 9/1997 | Jeffers | |
| 5,783,741 A * | 7/1998 | Ellis et al. | 72/23.39 |
| 5,932,791 A | 8/1999 | Hambitzer et al. | |
| 5,942,439 A | 8/1999 | Holt et al. | |
| 5,979,228 A | 11/1999 | Smith et al. | |
| 6,031,228 A * | 2/2000 | Abramson | 250/288 |
| 6,319,723 B1 | 11/2001 | Jeffers et al. | |
| 2002/0068017 A1 | 6/2002 | Naatz et al. | |

(Continued)

FOREIGN PATENT DOCUMENTS

CH     442 806     8/1965

(Continued)

OTHER PUBLICATIONS

ECLA key# at http://12.espacenet.com/espacenet/ecla/g01n/g01n30.htm, 4 pages.

(Continued)

*Primary Examiner*—Hezron Williams
*Assistant Examiner*—John Fitzgerald
(74) *Attorney, Agent, or Firm*—Dorsey & Whitney LLP

(57) ABSTRACT

The invention relates to a process and to an apparatus for providing gas for isotopic ratio analysis. According to the invention, a gas is generated from an eluate of a liquid chromatograph (LC). Subsequently, the gas is separated from the eluate. Finally, the gas is fed to an instrument (IRMS) for isotopic ratio analysis.

15 Claims, 1 Drawing Sheet

U.S. PATENT DOCUMENTS

2003/0228708 A1  12/2003  Huber et al.

FOREIGN PATENT DOCUMENTS

| | | |
|---|---|---|
| DE | 40 12 454 C1 | 8/1991 |
| DE | 93 14 169.6 | 2/1994 |
| DE | 43 33 208 A1 | 6/1994 |
| DE | 690 16 900 T2 | 6/1995 |
| DE | 44 13 197 A1 | 10/1995 |
| DE | 43 32 127 C2 | 1/1998 |
| DE | 196 50 444 A1 | 6/1998 |
| DE | 199 38 395 A1 | 2/2001 |
| DE | 199 56 632 C1 | 6/2001 |
| DE | 102 16 974.8 | 10/2002 |
| EP | 0 256 684 A2 | 2/1988 |
| EP | 0 306 332 B1 | 3/1989 |
| EP | 0 507 287 B1 | 10/1992 |
| EP | 0 509 316 A1 | 10/1992 |
| EP | 0 565 248 A2 | 10/1993 |
| EP | 0 729 577 B1 | 9/1996 |
| GB | 2 309 782 A | 6/1997 |
| JP | 1 983 0219 A | 2/1983 |
| JP | 6 102 0860 A | 1/1986 |
| JP | 0 126 2463 A | 10/1989 |
| WO | WO 97/31257 A1 | 2/1997 |
| WO | WO 0216927 2 | 2/2002 |

OTHER PUBLICATIONS

Yohannes Teffera, Josef J. Kusmierz, and Fred P. Abramson, "Continuous-Flow Isotope Ratio Mass Spectrometry Using the Chemical Reaction Interface with Either Gas or Liquid Chromatographic Introduction", Anal. Chem. 1996, 68, pp. 1888-1894.

W.A. Brand and P. Dobberstein, "Isotope-Ratio-Monitoring Liquid Chromatography Mass Spectrometry (IRM-LCMS): First Results From a Moving Wire Interface System", Isotopes Environ. Health Stud., 1996, vol. 32, pp. 275-283.

Brand W.A., et al., "New Methods for Fully Automated Isotope Ratio Determination From Hydrogen at the Natural Abundance Level", Isotopes Environ. Health Stud., Overseas Publishers Association (1996), vol. 32, pp. 263-273.

Coplen, Tyler B., et al., "Improvements in the Gaseous Hydrogen-Water Equilibration Technique for Hydrogen Isotope Ratio Analysis", Analytical Chemistry, vol. 63, No. 9, (May 1, 1991), pp. 911-912.

Epstein, S, et al., "Variation of $O^{18}$ Content of Waters from Natural Sources", Geochemicia et Cosmochimica Acta, vol. 4, (1953), pp. 213-224.

Finnigan Mat GmbH, "GasBench II: $^{18}$O-Equilibration on Water, Fruit Juice, and Wine", Finnigan MAT Application Flash Report No. G 30, 4 pages.

Horita, J., "Hydrogen Isotope Analysis of Natural Waters Using An H2-Water Equilibration Method: A Special Implication to Brines", Chemical Geology (Isotope Science Section), vol. 72. (1988), pp. 89-94.

Huber, C. et al., "Continuous Extraction of trapped Air from Bubble Ice or Water for On-Line Determination of Isotope Ratios", American Chemical Society, Analytical Chemistry, 10.1021/ac/0263972, pp. A-I.

Huber, C. et al. "Fast High-Precision On-Line Determination Of Hydrogen Isotope Ratios Of Water Or Ice By Continuous-Flow Isotope Ratio Mass Spectrometry", Rapid Communications in Mass Spectrometry, (2003), John Wiley & Sons, Ltd. 2003; vol. 17, pp. 1319-1325.

Leuenberger, M., et al., "On-Line Determination of Oxygen Isotope Ratios of Water or Ice by Mass Spectrometry", Analytical Chemistry, vol. 74, No. 18, (Sep. 15, 2002), pp. 4611-4617.

Sigg A., et al., "A Continuous Analysis Technique for Trace Species in Ice Cores", Environmental Science & Technology, vol. 28, No. 2, (1994), pp. 204-208.

\* cited by examiner

PROCESS AND APPARATUS FOR PROVIDING GAS FOR ISOTOPIC RATIO ANALYSIS

RELATED APPLICATION

This application claims priority to German Patent Application Serial Number 102 16 975.6, filed on Apr. 16, 2002, the disclosure of which is hereby incorporated by reference in its entirety.

BRIEF DESCRIPTION OF THE INVENTION

The invention relates to a process and to an apparatus for providing gas for isotopic ratio analysis.

BACKGROUND OF THE INVENTION

To carry out isotopic ratio analysis, high-precision mass spectrometers (IRMS) are used. They are fed with gaseous substances. Special considerations therefore have to be taken into account when analyzing solids or liquids. These may, for example, be provided as a mixture via a liquid chromatograph (LC). In the liquid chromatograph, the individual constituents of the liquid are separated with respect to time. One use of liquid chromatography is for substances which contain carbon, nitrogen and/or sulphur. For isotopic ratio determination of the substances mentioned, conversion to a gas is necessary. Suitable gases are typically $CO_2$, $N_2$ and $SO_2$.

Conventional processes for coupling liquid chromatography with an isotope mass spectrometer are based on substantially removing the eluent or solvent before the substance to be analyzed is converted to a gas. An example of such a process is the "moving wire" principle. In this process, the eluate leaving the liquid chromatograph is evaporated on a continuously moving wire and the remaining dry analysis substance is subsequently converted to a gas in an incineration reactor, see W. A. Brandt and P. Dobberstein: Isotope ratio monitoring liquid chromatography mass spectrometry (IRM-LCMS): First results from a moving wire interface system, Isotopes ENVIRON. HEALTH STUD., 1996, Vol. 32, 275–283.

A further process which has been used for coupling a liquid chromatograph to an isotope mass spectrometer is based on a desolvation of the eluate at semipermeable membranes and subsequent chemical reaction of the dry aerosol generated. (Continuous-Flow Isotope Ratio Mass Spectrometry Using the Chemical Reaction Interface with Either Gas or Liquid Chromatography Introduction, Yohannes Teffera, Josef J. Kusmierz and Fred P. Abramson, Anal. Chem., 1996, 68, 188–1894).

OBJECTS AND SUMMARY OF THE INVENTION

It is an object of the present invention to provide another process and another apparatus for providing gas for isotopic ratio analysis.

The process according to the invention is characterized by the following features:
a) gas is generated from an analysis substance dissolved in an eluate from a liquid chromatograph;
b) the gas is subsequently separated from the eluate,
c) finally, the gas is fed to an instrument for isotopic ratio analysis.

The individual process steps are in particular carried out continuously. According to the invention, and in contrast to the existing "moving wire" process, the gas is initially generated from the eluate of the liquid chromatograph (to be precise, from the analysis substances in the presence of the eluate) and then separated from the eluate. The gas contains the isotopes to be analyzed. Generation of the gas directly from the eluate reduces the possibility of isotope fractionation. The process can also be carried out using relatively simple apparatus.

Advantageously, the gas is generated chemically from the eluate, for example by adding a reagent to the eluate. One possible such reagent may be ammonium persulphate.

It is also possible to react the eluate at high temperature with an oxidizing agent, e.g. copper oxide. In this case, the eluate is completely evaporated before the reaction and condensed again afterwards.

It is also possible to physically generate the gas from the eluate, for instance by heating. By its nature, this also depends on the properties of the constituents of the eluate.

It is likewise possible to generate the gas from the eluate using a catalyst. A preferred catalyst is platinum.

It will be appreciated that it is also possible to combine the means of gas generation described, for instance heating in the presence of a catalyst and/or adding a reagent with subsequent heating and/or irradiation, the latter, for example, with ultraviolet light.

A further advantageous embodiment of the invention contemplates separating the gas from the eluate at a membrane. The membrane is preferably gas-permeable and liquid-impermeable. The principle of such a separation is described, for example, in U.S. Pat. No. 4,886,528.

Preference is given to combining the removed gas with a carrier gas and feeding them together to an instrument for isotopic ratio analysis, especially an isotopic ratio mass spectrometer (IRMS).

The invention further contemplates the addition of a carrier gas to the eluate before or after gas generation.

An apparatus for providing gas for isotopic ratio analysis has the following features:
a) a liquid chromatograph is coupled to a unit for generating gas from the eluate of the liquid chromatograph (gas generating unit),
b) the gas generating unit is coupled to a unit for separating the gas (gas separating unit) from the eluate,
c) the gas separating unit is coupled via a unit for feeding gas (gas feed unit) to a device for isotopic ratio analysis.

BRIEF DESCRIPTION OF THE DRAWINGS

Further features of the invention can be determined from the description and from the main claims. Implementation examples of the invention are illustrated in detail hereinbelow with reference to the single drawing which shows a system for carrying out the invention.

DESCRIPTION OF THE PREFERRED EMBODIMENT(S)

Figure 1:
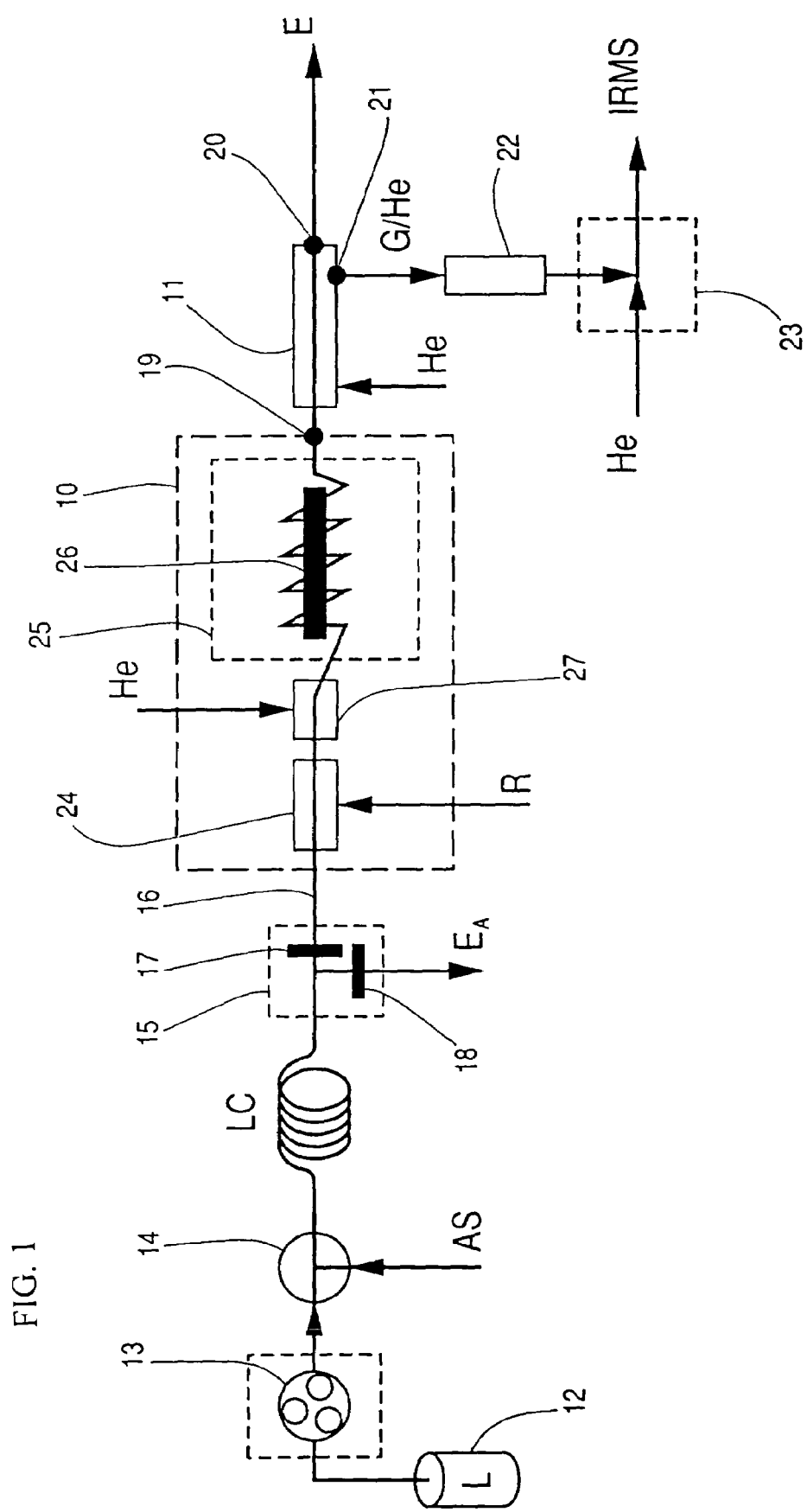

An apparatus according to the invention for providing gas for isotopic ratio analysis in particular has a liquid chromatograph LC, a gas generating unit 10 and a gas separating unit 11.

The liquid chromatograph may be replaced by a pump and an injection loop if no chromatographic separation is desired.

A vessel 12 for a liquid eluent or solvent is located upstream of the liquid chromatograph LC is in this case disposed. Although a solution does not necessarily have to be present, reference is made hereinbelow to the solvent L for the sake of simplicity.

The solvent L is removed from the vessel 12 with the aid of a pump 13. Downstream of the pump 13 is provided a feed 14, through which a substance to be analyzed AS may be added to the solvent L before entry into the liquid chromatograph LC. It will be appreciated that the solvent L may already contain the substance to be analyzed in the vessel 12.

The liquid leaving the liquid chromatograph LC is referred to as eluate. A portion thereof may be removed via a branch 15 disposed downstream of the liquid chromatograph LC. The aim may be to control the volume stream in a line 16 downstream of the branch 15. To this end, the branch 15 may have suitable flow resistors 17, 18, throttles, valves or the like. The portion of the eluate which has been branched off at this point (and thus the portion which does not flow through the line 16) is referred to in the drawing as EA.

The eluate flowing along the line 16 is treated in the gas generating unit 10 in a way which leads to the formation of gas. At an exit 19 of the gas generating unit 10, there is then a mixture of eluate and gas. This is then continuously separated in the gas separating unit 11 at a membrane, so that eluate E without gas (optionally together with a residue of a reagent) leaves the gas separating unit via an outlet 20, and a gaseous component leaves via an outlet 21.

In the region of the gas separating unit 11, a carrier gas may be added, so that the volume stream at the outlet 21 is increased. Accordingly, the gaseous component at the outlet 21 then contains the gas G together with the carrier gas. The carrier gas provided is preferably helium (He). The gas mixture leaving at the outlet 21 is therefore referred to in the diagram as G/He.

Downstream of the outlet 21 is disposed a cold trap 22 for freezing out a residual content of liquid. This is especially true when using an aqueous eluate.

Downstream of the cold trap 22 is provided an open split 23. It is again possible there to adjust the volume stream and optionally effect a dilution before the gas (comprising more or less carrier gas) is fed to an isotopic ratio mass spectrometer IRMS. In this case, the open split 23 functions as a gas feed unit for the IRMS.

In the gas generator unit 10, various process steps may be carried out and different apparatus parts may be provided. The aim is to generate a gas which contains the isotopic information of interest.

The gas generation may be initiated by chemical reaction. In the drawing, a feed unit 24 for a reagent R is provided. Downstream of the feed unit 24 is a reaction zone 25. In this zone, there may additionally be a thermal treatment or an irradiation, for instance with UV light. A UV lamp is referred to in the diagram by the number 26. In the reaction zone 25, catalytically active material may be provided.

Alternatively or additionally to the carrier gas feed in the region of the gas separating unit 11, carrier gas may also be fed at another point, for instance in the gas generating unit 10, in particular between the feed unit 24 and the reaction zone 25, see feed 27.

Between the liquid chromatograph LC and the feed unit 24, a UV detector may additionally be provided. The UV detector may be used to record a chromatogram directly downstream of the liquid chromatograph LC.

In one application example, a glucose sample dissolved in water is injected into an HPLC system (HP=high performance), via the feed 14 in the apparatus shown. The solvent used (mobile HPLC phase) is water or a mixture of water/inorganic buffer. The mixture of substance to be analyzed and mobile phase is resolved with respect to time in the liquid chromatograph LC.

An aqueous persulphate solution as a reagent is added on-line or continuously to the eluate via the feed unit 24. The organic substances contained in the eluate are in turn at least continuously converted to $CO_2$ in the reaction zone 25.

The $CO_2$ is removed in the gas separating unit 11, removed by the helium carrier gas and fed to the open split 23. Instead of the cold trap 22, a nafion tube (known by this term) may be provided.

The gas/carrier gas mixture is fed through the open split 23 to the IRMS mass spectrometer. The isotopic ratios, for example of $13C/12C$, of the individual substances are analyzed there.

Instead of the gas separating unit 11 shown, in which the gas exits through a liquid-impermeable membrane, other processes for converting the resulting gases into a carrier gas stream (helium stream) are conceivable, for instance using an evaporating chamber or a spray chamber (physical separation of gas, water and reagent) with subsequent membrane transfer or subsequent drying.

The analysis of the substances carried out in the mass spectrometer is effected with substantial retention of the resolution of the substances with respect to time provided by the liquid chromatograph LC.

LIST OF DESIGNATIONS

10 gas generating unit
11 gas separating unit
12 vessel
13 PUMP
14 inlet
15 branch
16 line
17 flow resistor
18 flow resistor
19 exit
20 outlet
21 outlet
22 cold trap
23 open split
24 feed unit
25 reaction zone
26 UV lamp
27 feed
AS substance to be analyzed
EA branched-off eluate
G/He gas/carrier gas
IRMS isotropic ratio mass spectrometer
L solvent
LC liquid chromatograph

The invention claimed is:

1. A process for providing gas for isotopic ratio analysis, comprising the steps of:
   a) generating gas from an analysis substance dissolved in a liquid eluate from a liquid chromatograph,
   b) subsequently separating the gas from the liquid eluate, wherein the gas is conveyed to an isotope ratio mass spectrometer for isotopic ratio analysis.

2. The process according to claim 1, characterized in that the gas is generated using a catalyst.

3. The process according to claim 1, characterized in that the gas is separated from the eluate at a membrane in a gas separating unit.

4. The process according to claim 1, characterized in that a carrier gas is added to the gas and they are fed together for isotopic ratio analysis.

5. The process according to claim 1, characterized in that carrier gas is added to the liquid eluate.

6. The process according to claim 1, characterized in that the analysis substance is an organic substance and the generated gas is $CO_2$.

7. The process according to claim 1, characterized in that the gas is generated chemically.

8. The process according to claim 1 or 7, characterized in that the gas is generated physically.

9. An Apparatus for providing gas for isotopic ratio analysis, comprising:
   a) a liquid chromatograph, said liquid chromatograph generating a liquid eluate;
   b) a gas generating unit coupled to the liquid chromatograph, said gas generating unit for generating gas from an analysis substance present in the liquid eluate, and
   c) a gas separating unit coupled to said gas generating unit for separating the gas from the liquid eluate, and configured to supply the separated gas to an isotope ratio mass spectrometer for isotopic ratio analysis of the gas.

10. The apparatus according to claim 9, characterized in that the liquid chromatograph contains no separating column and consists only of pump and injection unit.

11. The apparatus of claim 9 further comprising a gas feed unit coupling said separating unit to an isotope ratio mass spectrometer for isotopic ratio analysis of the gas.

12. The apparatus of claim 9 wherein the gas generating unit further comprises a feed unit configured to provide a reagent and a reaction zone coupled to the feed unit.

13. The apparatus of claim 12 wherein said reaction zone further comprises a thermal or irradiation treatment device.

14. A process of analyzing a substance in an isotope ratio mass spectrometer, where the substance is present in a liquid eluate received from a liquid chromatograph, characterized in that: the substance while present in the liquid eluate is converted to a gas, the gas is separated from the liquid elute, and said separated gas is analyzed in an isotope ratio mass spectrometer to determine the isotope ratio of the gas.

15. The process of claim 14 wherein the substance is an organic sample, and further comprising the steps of adding a persulphate solution to the liquid eluate to convert the organic substance to $CO_2$ gas, separating the $CO_2$ gas from the liquid eluate and conveying the $CO_2$ gas to an isotope ratio mass spectrometer for isotopic ratio analysis of the $CO_2$ gas.

* * * * *